US007357142B2

(12) United States Patent
Merkle

(10) Patent No.: US 7,357,142 B2
(45) Date of Patent: Apr. 15, 2008

(54) APPARATUS FOR CONTINUOUSLY ASPIRATING A FLUID FROM A FLUID SOURCE

(75) Inventor: William L. Merkle, Elizabeth, IL (US)

(73) Assignee: MD Technologies inc., Galena, IL (US)

( * ) Notice: Subject to any disclaimer, the term of this patent is extended or adjusted under 35 U.S.C. 154(b) by 223 days.

(21) Appl. No.: 11/027,800

(22) Filed: Dec. 31, 2004

(65) Prior Publication Data
US 2006/0144440 A1    Jul. 6, 2006

(51) Int. Cl.
*B67C 3/16* (2006.01)
(52) U.S. Cl. ............... 137/1; 137/101.25; 137/205; 137/256; 141/198; 604/35; 604/320
(58) Field of Classification Search ............... 137/205, 137/255, 256, 101.25, 101.27, 208, 110, 112, 137/87.02, 202, 1; 141/65, 95, 198, 323, 141/324; 604/35, 318–320, 323, 324, 326; 222/36
See application file for complete search history.

(56) References Cited

U.S. PATENT DOCUMENTS

| | | | | |
|---|---|---|---|---|
| 3,181,729 | A * | 5/1965 | Milonas et al. ............... 222/36 |
| 3,699,815 | A | 10/1972 | Holbrook ...................... 73/427 |
| 3,705,598 | A * | 12/1972 | Ray ....................... 137/101.25 |
| 3,855,997 | A | 12/1974 | Sauer .......................... 128/2 F |
| 3,965,902 | A | 6/1976 | Reilly et al. ................. 128/276 |
| 4,228,798 | A | 10/1980 | Deaton ........................ 128/276 |
| 4,312,351 | A | 1/1982 | Kurtz et al. ................. 128/276 |
| 4,384,580 | A | 5/1983 | Leviton ....................... 604/119 |
| 4,388,922 | A | 6/1983 | Telang ......................... 604/319 |
| 4,643,197 | A | 2/1987 | Greene et al. ............... 128/762 |
| 4,704,106 | A | 11/1987 | Shave et al. ................. 604/319 |
| 5,133,374 | A | 7/1992 | Druding et al. ........... 134/104.2 |
| 5,286,262 | A | 2/1994 | Herweck et al. ............ 604/321 |
| 5,575,293 | A | 11/1996 | Miller et al. ................. 128/752 |
| 5,624,418 | A | 4/1997 | Shepard ....................... 604/319 |
| 5,720,299 | A | 2/1998 | Theodoru .................... 128/760 |
| 5,792,126 | A | 8/1998 | Tribastone et al. .......... 604/319 |
| 6,152,902 | A | 11/2000 | Christian et al. ........... 604/320 |
| 6,513,187 | B1 * | 2/2003 | Naseth, Sr. .................... 15/314 |
| 6,652,495 | B1 * | 11/2003 | Walker ........................ 604/319 |

* cited by examiner

*Primary Examiner*—Ramesh Kirshnamurthy
*Assistant Examiner*—Craig Price
(74) *Attorney, Agent, or Firm*—Pauley Petersen & Erickson

(57) ABSTRACT

An apparatus for continuously aspirating a fluid from a fluid source. A vacuum source is operatively connected to a first container forming a first chamber and a second container forming a second chamber. A fluid collection tube provides communication between the fluid source and each of the first chamber and the second chamber. A first level sensor is positioned within the first chamber and a second level sensor is positioned within the second chamber. Upon receiving a signal generated by one of the first level sensor and the second level sensor, a relay responsively exposes a vacuum within one of the first chamber and the second chamber to continuously aspirate at least a portion of the fluid from the fluid source. A shut-off valve is preferably positioned within each of the first chamber and the second chamber to prevent communication between the vacuum source and the corresponding chamber with a fluid level within the chamber at a fluid level setpoint.

10 Claims, 3 Drawing Sheets

US 7,357,142 B2

APPARATUS FOR CONTINUOUSLY ASPIRATING A FLUID FROM A FLUID SOURCE

BACKGROUND OF THE INVENTION

1. Field of the Invention

This invention relates to an apparatus and method for continuously aspirating a fluid from a fluid source.

2. Discussion of Related Art

During surgical procedures, a medical instrument, for example an endoscope, may be inserted into an interior area of the patient's body to remove bodily fluids, which may contain potentially infectious or harmful fluid materials. These fluids, which may include small particles, are drawn through the instrument and are collected within a container using a vacuum or suction source. In many conventional apparates, when the container is filled, the procedure is interrupted in order to empty the container of the collected fluid. Typically, the collected fluid is deposited locally within a larger container. After the container has been emptied, the procedure can continue until the container is once again filled. This process requires operators to handle the fluid, thereby subjecting the operators to potentially infectious or harmful fluid materials.

Additionally, some conventional apparates include an externally mounted shut-off valve, which shuts off the vacuum source to the apparatus if the container overflows with fluid. The apparatus will not function until the container is emptied of the fluid. External shut-off valves further subject operators to potentially infectious or harmful fluid materials.

SUMMARY OF THE INVENTION

It is one object of this invention to provide an apparatus and method for continuously aspirating a fluid from a fluid source.

It is another object of this invention to provide an apparatus for collecting the aspirated fluid at a remote location without the need for operator contact or exposure to potentially dangerous or harmful fluid materials.

It is yet another object of this invention to provide an internally mounted shut-off valve to monitor the fluid collection for overflow while eliminating the need for operator action, whereby operator contact with or exposure to potentially dangerous or harmful fluid materials is prevented.

The above and other objects of this invention can be attained through an apparatus for continuously aspirating a fluid from a fluid source. The apparatus includes a first container forming a chamber. A vacuum source is operatively connected to the first container and includes a first vacuum tube exposed to or extending into the chamber. A first level sensor is positioned within the chamber to monitor a fluid level within the chamber. A first fluid collection tube extends into the chamber and is operatively connectable to an aspirator device, thereby providing communication between the fluid source and the chamber. A first solenoid valve connects the first container to the vacuum source, and is activatable to provide communication between the vacuum source and the chamber. A relay is in electrical communication with the first solenoid valve and activates the first solenoid valve to move to an open position. With the first solenoid valve in the open position, a vacuum is exposed within the chamber to aspirate at least a portion of the fluid from the fluid source to within the chamber. A first shut-off valve is positioned within the chamber and prevents communication between the vacuum source and the chamber with a fluid level within the chamber at a fluid level setpoint.

This invention further comprehends an apparatus for continuously aspirating a fluid from a fluid source including a vacuum source. A first container forms a first chamber and is operatively connected to the vacuum source. A first level sensor senses a level of the fluid within the first chamber. A second container forming a second chamber is operatively connected to the vacuum source. A second level sensor senses a level of the fluid within the second chamber. A fluid collection tube provides communication between the fluid source and each of the first chamber and the second chamber. A relay receives at least one signal from at least one of the first level sensor and the second level sensor, and responsively exposes a vacuum within one of the first chamber and the second chamber to continuously aspirate at least a portion of the fluid from the fluid source.

This invention still further comprehends a method for continuously aspirating a fluid from a fluid source. At least a portion of the fluid from the fluid source is aspirated into a first chamber formed by a first container. The first chamber is in communication with a vacuum source. The aspirated fluid is collected within the first container until a fluid level within the first chamber approaches a fluid level setpoint. A first solenoid valve is closed to prevent communication between the vacuum source and the first chamber and a second solenoid valve is opened to provide communication between the vacuum source and a chamber formed by a second container. The second chamber is in communication with the vacuum source. At least a portion of the fluid is aspirated from the fluid source and into the second chamber, as the aspirated fluid collected in the first container is drained into a drain pipe.

Other objects and advantages of this invention are apparent to those skilled in the art, in view of the following detailed description taken in conjunction with the appended claims and drawings.

DETAILED DESCRIPTION OF THE INVENTION

This invention provides an apparatus for aspirating a fluid from a fluid source. Suction is employed to collect the fluid within one or more containers and, by interrupting the suction within a selected container, the collected or aspirated fluid can be drained through a drain pipe to a remote site. Preferably, the apparatus includes a plurality of containers that can be selectively filled with aspirated fluid collected from the fluid source. As one container is used to collect the aspirated fluid, the aspirated fluid collected in another container is drained to the remote site, thus, providing an apparatus and method for continuously aspirating a fluid from a fluid source. For example, the apparatus can be used with a medical instrument or tool, such as an endoscope, to remove bodily fluids, including small particles, from an internal area of an animal body or a human body.

Figure 1:
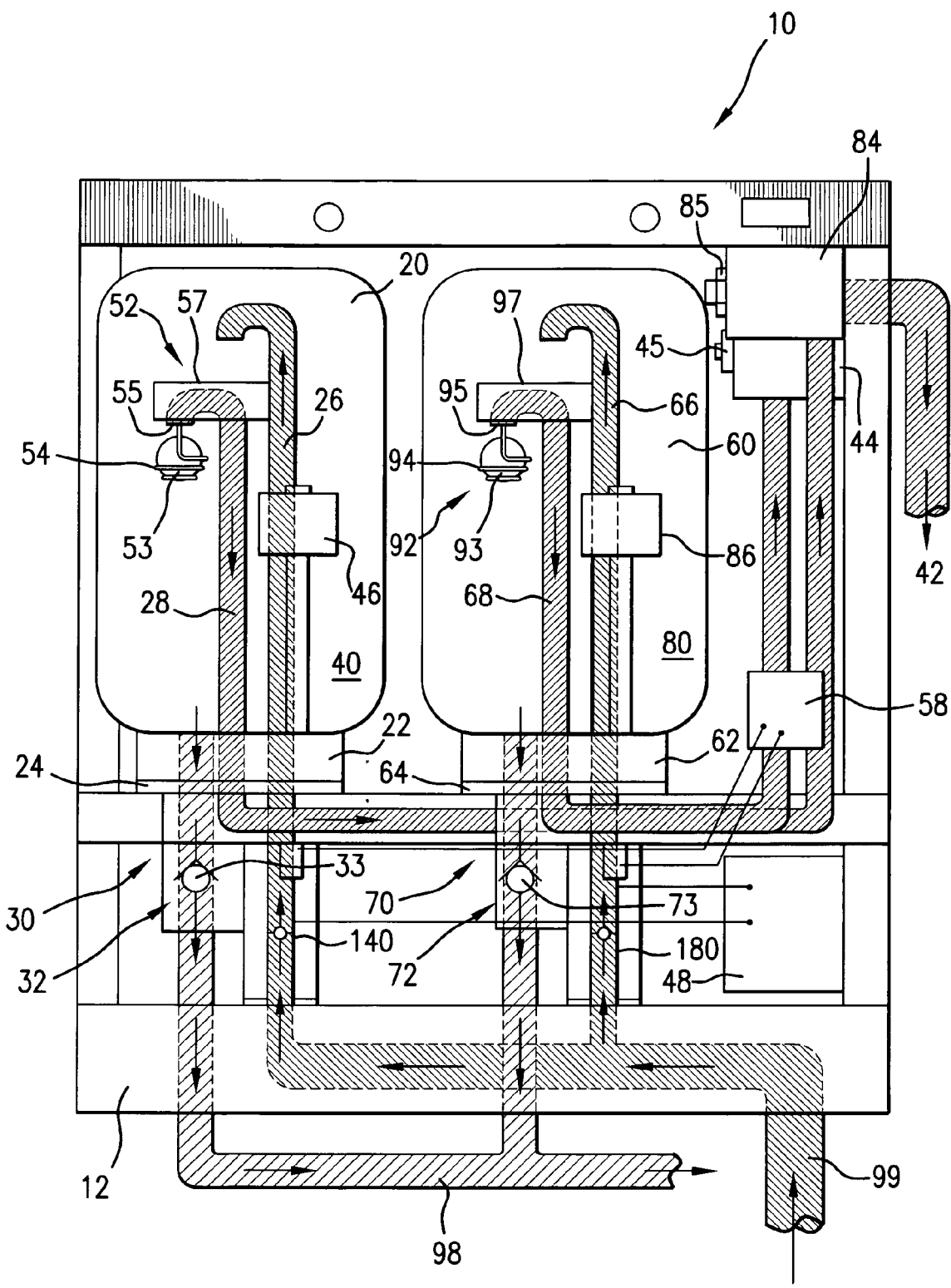
FIG. 1 is a diagrammatic partial sectional side view of an apparatus with a side enclosure panel removed, according to one preferred embodiment of this invention.
Figure 2:
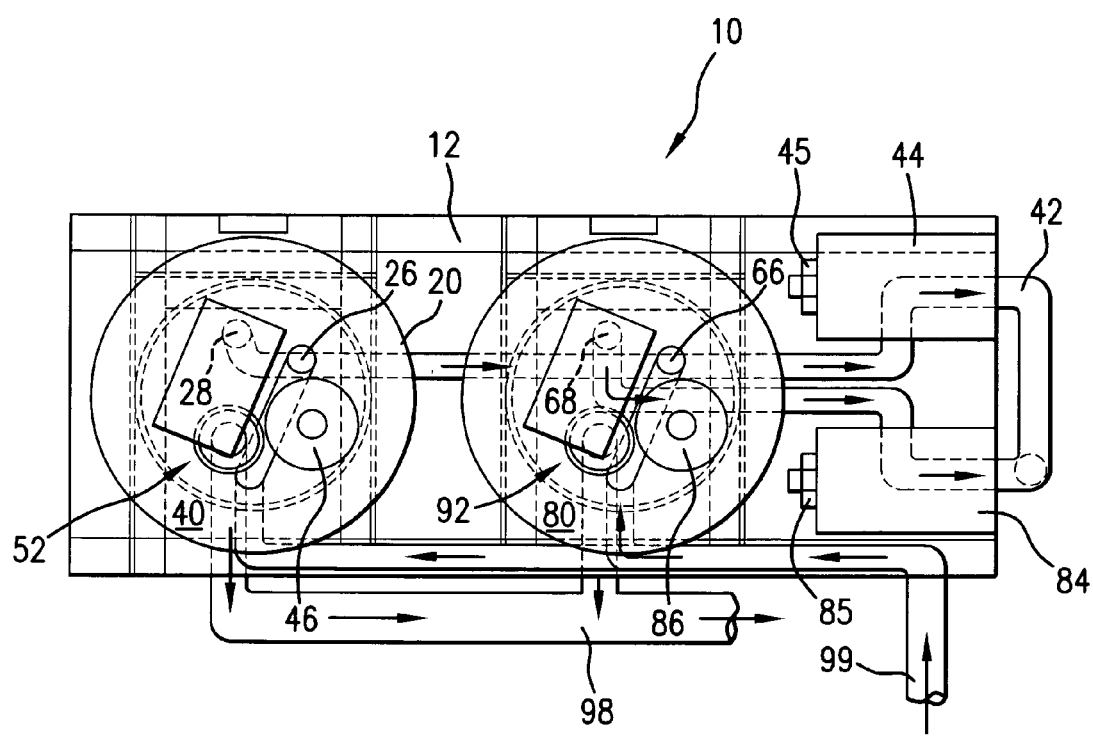
FIG. 2 is a diagrammatic partial sectional top view of the apparatus shown in FIG. 1 with a top enclosure panel removed.
Figure 3:
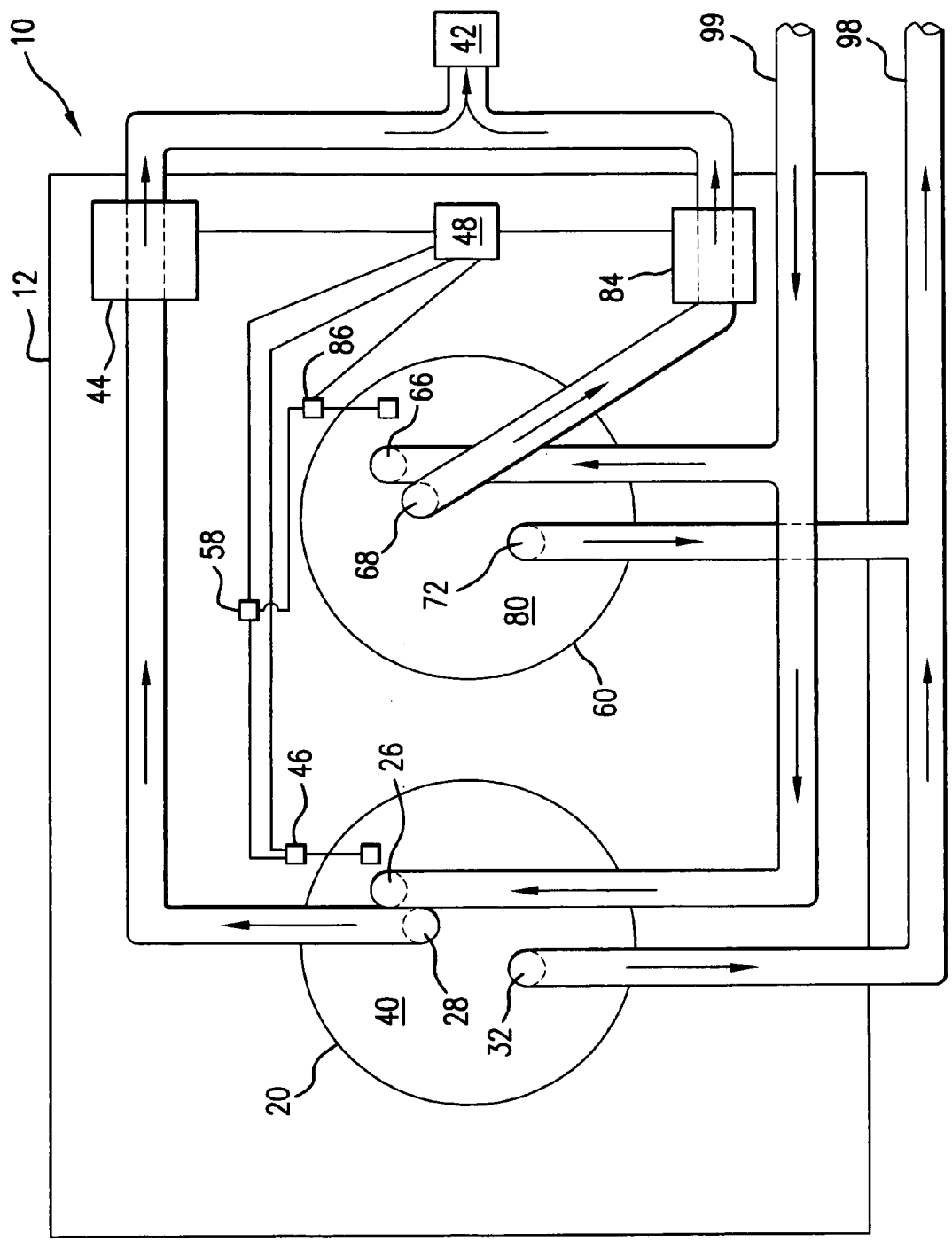
FIG. 3 is a schematic top view of an apparatus showing fluidic communication and/or electrical communication between various elements and/or components of the apparatus, according to one preferred embodiment of this invention.

Referring to FIGS. 1-3, apparatus 10 for continuously aspirating a fluid from a fluid source includes an enclosure 12 preferably fabricated of a metal material or other suitable material for a particular application. FIG. 1 shows apparatus 10 with a side enclosure panel removed and FIG. 2 shows apparatus 10 with a top enclosure panel removed, in order to show various elements and/or components of apparatus 10. FIG. 3 shows fluidic communication between various elements and/or components of apparatus 10, for example using a suitable pipe and/or a flexible tube or hose, and electrical communication between various elements and/or components of apparatus 10, represented as a single solid line, using a suitable electrical connection such as a wire. In one preferred embodiment of this invention, with the elements and/or components of apparatus 10 housed within enclosure 12, apparatus 10 can be mounted to a wall or other suitable support.

A first container 20 is housed within enclosure 12 and has a cover 22 removably attachable to an open end portion of container 20. Container 20 can have any suitable size and/or shape to accommodate the inner elements and/or components of apparatus 10 discussed below. Preferably, but not necessarily, container 20 is reusable.

As shown in FIG. 1, a base or plate 24 is attached to or integrated with cover 22. Plate 24 includes a first fluid collection tube 26, a first vacuum tube 28 and a fitting 30 for connecting a drainage assembly 32 to container 20. In one preferred embodiment of this invention, drainage assembly 32 includes a first drain valve 33 positioned within an opening formed by fitting 30 in container 20 to provide communication between a chamber 40 defined or formed by container 20 and a drain pipe 98 connected to first drain valve 33. With an internal pressure of container 20 at a determined level, drain valve 33 opens to allow the aspirated fluid collected within chamber 40 to flow into drain pipe 98 and be directed to a remote location or site for disposal. Drain valve 33 preferably includes a check valve or a ball valve, although any suitable drain valve assembly or one-way valve known in the art may be used in drainage assembly 32. Apparatus 10 may include any additional suitable element and/or component, such as disclosed in U.S. Pat. No. 5,133,374 issued to Druding et al. on 28 Jul. 1992, the entire disclosure of which is incorporated herein by reference.

Each of fluid collection tube 26 and vacuum tube 28 is in communication with chamber 40. As shown in FIG. 1, each of fluid collection tube 26 and vacuum tube 28 may extend through plate 24 and into chamber 40. Preferably, fluid collection tube 26 has a first end portion that extends into chamber 40 and a second end portion operatively connectable to a medical instrument or tool, such as an aspirator device (not shown). In one preferred embodiment of this invention as shown in FIG. 1, fluid collection tube 26 is connected to a main fluid collection tube 99, which is connectable to the aspirator device. Fluid collection tube 26 provides communication between the fluid source and chamber 40.

A vacuum source 42 is operatively connected to container 20. As shown in FIG. 1, vacuum tube 28 has a first end portion that extends into chamber 40 and a second end portion operatively connected to vacuum source 42. The first end portion extending into chamber 40 preferably terminates short of the first end portion of fluid collection tube 26, as shown in FIG. 1. Vacuum tube 28 provides communication between vacuum source 42 and chamber 40. Preferably, a first solenoid valve 44, as shown in FIG. 2, connects container 20 to vacuum source 42 and is activatable to provide communication between vacuum source 42 and first chamber 40. Solenoid valve 44 can be connected between vacuum tube 28 and vacuum source 42. Solenoid valve 44 is movable between an open position and a closed position. In the open position, solenoid valve 44 provides communication between vacuum source 42 and chamber 40. In the closed position, solenoid valve 44 prevents communication between vacuum source 42 and chamber 40. Other suitable valves known in the art can be used to operatively connect vacuum source 42 to container 20.

A first level sensor 46 senses a level of the fluid within chamber 40. In one preferred embodiment of this invention, level sensor 46 is positioned within chamber 40. Level sensor 46 is preferably connected with respect to fluid collection tube 26 and positioned at a determined or desired location with respect to cover 22 in order to monitor and/or measure a volume of aspirated fluid collected within container 20. A relay 48 is positioned with respect to container 20 and in electrical communication with level sensor 46 and a first solenoid 45 controlling a movement of solenoid valve 44. Relay 48 receives a signal transmitted from level sensor 46 and, in response to the received signal, activates solenoid valve 44. For example, relay 48 transmits a signal to solenoid 45 to open solenoid valve 44. With solenoid valve 44 in the open position, a suction or vacuum is exposed within chamber 40 to aspirate at least a portion of the fluid from the fluid source to within chamber 40. Conversely, in response to a signal transmitted by level sensor 46 to relay 48 indicating that a fluid level within chamber 40 has reached or is approaching a fluid level setpoint, relay 48 transmits a signal to solenoid 45 to close solenoid valve 44. With solenoid valve 44 in the closed position, communication between vacuum source 42 and chamber 40 is prevented.

For example, level sensor 46 may transmit a stop signal to relay 48 with the fluid level within chamber 40 approaching the fluid level setpoint. Upon receiving the stop signal transmitted from level sensor 46, relay 48 responsively transmits a signal to solenoid 45, which closes solenoid valve 44 to prevent communication between vacuum source 42 and chamber 40. Further, in one preferred embodiment of this invention, relay 48 transmits a second signal to a second solenoid 85, which opens a second solenoid valve 84 to provide communication between vacuum source 42 and a second chamber 80, as discussed in greater detail below. With solenoid valve 44 closed, the fluid within chamber 40 is drained through drainage assembly 32 and into drain pipe 98.

In one preferred embodiment of this invention, apparatus 10 includes an internal shut-off valve positioned within chamber 40. An internal shut-off valve provides several advantages over conventional externally mounted shut-off valves, such as the elimination of any required operator action. The elimination of operator action isolates the operator from contact or exposure to the aspirated fluid, which may contain infectious or harmful fluid materials and/or medical waste.

As shown in FIG. 1, a first shut-off valve 52 is positioned within chamber 40 and prevents communication between vacuum source 42 and chamber 40 with the fluid level within chamber 40 at the fluid level setpoint, such as to prevent fluid overflow. Preferably, shut-off valve 52 includes a check valve or a ball valve. In one preferred embodiment of this invention, shut-off valve 52 includes a ball float 53 freely positioned within a retainer 54. Retainer 54 is connected with respect to vacuum tube 28 using a suitable connector, such as a retainer bolt or screw. Ball float 53 is responsively positionable over a seat 55 formed in a valve body 57 positioned at and connected to the first end portion of vacuum tube 28, as shown in FIG. 1, with the fluid level within chamber 40 at the fluid level setpoint. Thus, ball float 53 retained within retainer 54 is permitted to respond to fluid level changes within chamber 40. For example, as the fluid level rises to the fluid level setpoint, ball float 53 floats with a fluid level surface and is drawn into seat 55 by the vacuum or suction within vacuum tube 28, thereby preventing fluid flow into vacuum tube 28. Other suitable valve assemblies known in the art may be used in shut-off valve 52. With shut-off valve 52 preventing communication between vacuum source 42 and chamber 40, at least a portion of the fluid contained within container 20 is drained through drainage assembly 32.

In one preferred embodiment of this invention, apparatus 10 includes a counter 58 or other suitable flow meter for measuring or calculating a total fluid volume passed through apparatus 10 from the fluid source into drain pipe 98. Preferably, counter 58 is operatively connected to level sensor 46 and is activated as level sensor 46 transmits each stop signal to relay 48. Counter 58 counts or records each instance that chamber 40 is filled with aspirated fluid to the fluid level setpoint, before the aspirated fluid is drained from chamber 40. Counter 58 can include a local display to indicate the volume of aspirated fluid collected and passed through chamber 40. Alternatively, counter 58 can send a signal to a remote processor, for example which records the volume of aspirated fluid passing through chamber 40.

Apparatus 10 preferably includes a second container 60 housed within enclosure 12. Preferably, but not necessarily, second container 60 and its elements and/or components are the same or similar to first container 20 and its corresponding elements and/or components. As shown in FIG. 1, container 60 has a cover 62 removably attachable to an open end portion of container 60. Container 60 can have any suitable size and/or shape to accommodate the inner elements and/or components of apparatus 10 positioned within container 60, discussed below. As shown in FIG. 1, a base or plate 64 is attached to or integrated with cover 62. Plate 64 includes a second fluid collection tube 66, a second vacuum tube 68 and a fitting 70 for connecting a drainage assembly 72 to container 60. In one preferred embodiment of this invention, drainage assembly 72 includes a second drain valve 73 positioned within an opening formed by fitting 70 in container 60 to provide communication between a chamber 80 formed or defined by second container 60 and drain pipe 98 connected to drain valve 73. With an internal pressure of container 60 at a determined pressure, drain valve 73 opens to allow the aspirated fluid collected within chamber 80 to flow into drain pipe 98 to the remote location or site for disposal. Second drain valve 73 preferably but not necessarily is the same or similar to first drain valve 33.

In one preferred embodiment of this invention, each of drainage assembly 32 and drainage assembly 72 is connected to or includes a P-trap or water seal. The P-trap and/or drainage assembly 32 or drainage assembly 72 can be replaced by a solenoid valve, a spring-loaded check valve or another suitable valve device known to those skilled in the art.

Each of fluid collection tube 66 and vacuum tube 68 is in communication with chamber 80. As shown in FIG. 1, each of fluid collection tube 66 and vacuum tube 68 may extend through plate 64 and into chamber 80. Preferably, fluid collection tube 66 has a first end portion that extends into chamber 80 and a second end portion operatively connectable to the aspirator device. Fluid collection tube 66 provides communication between the fluid source and chamber 80. Preferably, first fluid collection tube 26 and second fluid collection tube 66 extend from or connect to main fluid collection tube 99, as shown in FIG. 1. In this preferred embodiment of this invention, main collection tube 99 is removably connectable to a medical instrument or tool, such as an aspirating device (not shown). Preferably, a first inlet check valve 140 is positioned within first fluid collection tube 26, for example at the connection between main fluid collection tube 99 and first fluid collection tube 26 to prevent fluid flow from within chamber 40. Similarly, a second inlet check valve 180 is positioned within second fluid collection tube 66 to prevent fluid flow from within chamber 80. Further, each of first inlet check valve 140 and second inlet check valve 180 prevents air from being vacuumed or suctioned out of chamber 80 and chamber 40, respectively.

Vacuum source 42 is operatively connected to second container 60. As shown in FIG. 1, vacuum tube 68 has a first end portion that extends into chamber 80 and a second end portion operatively connected to vacuum source 42. The first end portion extending into chamber 80 preferably terminates short of the first end portion of fluid collection tube 66. Vacuum tube 68 provides communication between vacuum source 42 and chamber 80. Preferably, a second solenoid valve 84 connects second container 60 to vacuum source 42 and is activatable to provide communication between vacuum source 42 and second chamber 80. Preferably, solenoid valve 84 is connected between vacuum tube 68 and vacuum source 42. Solenoid valve 84 is movable between an open position and a closed position. In the open position, solenoid valve 84 provides communication between vacuum source 42 and chamber 80. In the closed position, solenoid valve 84 prevents communication between vacuum source 42 and chamber 80.

A second level sensor 86 senses a level of the fluid within chamber 80. In one preferred embodiment of this invention, level sensor 86 is positioned within chamber 80. Level sensor 86 is preferably connected with respect to fluid collection tube 66 and positioned at a determined or desired location with respect to cover 62 in order to monitor and/or measure a volume of aspirated fluid collected within container 60. Relay 48 is positioned with respect to container 60 and in electrical communication with level sensor 86 and a solenoid 85 controlling a movement of solenoid valve 84. Relay 48 receives a signal transmitted from level sensor 86 and, in response to the received signal, transmits a signal to solenoid 85 to open solenoid valve 84. With solenoid valve 84 in the open position, a suction or vacuum is exposed within chamber 80 to aspirate at least a portion of the fluid from the fluid source to within chamber 80. Conversely, in response to a signal transmitted by level sensor 86 to relay 48 indicating that a fluid level within chamber 80 has reached or is approaching a fluid level setpoint, relay-48 transmits a signal to solenoid 85 to close solenoid valve 84. With solenoid valve 84 in the closed position, communication between vacuum source 42 and chamber 80 is prevented.

For example, level sensor 86 may transmit a stop signal to relay 48 with the fluid level within chamber 80 approaching the fluid level setpoint. Upon receiving the stop signal transmitted from level sensor 86, relay 48 responsively transmits a signal to solenoid 85, which closes solenoid valve 84 to prevent communication between vacuum source 42 and chamber 80. Preferably, relay 48 transmits a second signal to solenoid 45, which opens first solenoid valve 44 to provide communication between vacuum source 42 and first chamber 40. A vacuum is exposed within chamber 40 to aspirate at least a portion of the fluid from the fluid source to within chamber 40. With solenoid valve 84 closed, the fluid within chamber 80 is drained through drainage assembly 72.

Thus, relay 48 is capable of receiving signals from first level sensor 46 and second level sensor 86, and responsively initiating a vacuum within first chamber 40 or second chamber 80 to continuously aspirate at least a portion of the fluid from the fluid source. In addition, upon receiving the signal from the level sensor 46 or 86, relay 48 closes first solenoid valve 44 or second solenoid valve 84, thereby preventing communication between vacuum source 42 and the other chamber. Without communication between vacuum source 42 and the other chamber, the fluid within the other chamber is allowed to drain from the chamber into drain pipe 98.

In one preferred embodiment of this invention, apparatus 10 includes an internal shut-off valve positioned within chamber 80. As shown in FIG. 1, a second shut-off valve 92 is positioned within chamber 80 and prevents communication between vacuum source 42 and chamber 80 with the fluid level within chamber 80 at the fluid level setpoint. Preferably, second shut-off valve 92 is the same or similar to first shut-off valve 52 positioned within chamber 40. For example, in one preferred embodiment of this invention, shut-off valve 92 includes a ball float 93 freely positioned within a retainer 94. Retainer 94 is connected with respect to vacuum tube 68 using a suitable connector, such as a retainer bolt or screw. Ball float 93 is responsively positionable over a seat 95 formed in a valve body 97 positioned at and connected to the first end portion of vacuum tube 68, as shown in FIG. 1, with the fluid level within chamber 80 at the fluid level setpoint.

Preferably, counter 58 is also operatively connected to second level sensor 86 and is activated as level sensor 86 transmits each stop signal to relay 48. Alternatively, a second counter (not shown), preferably the same or similar to counter 58, can be operatively connected to second level sensor 86 to count or record each instance that chamber 80 is filled with aspirated fluid to the fluid level setpoint, independently of counter 58 operation.

In one preferred embodiment of this invention, apparatus 10 can be used for continuously aspirating a fluid from a fluid source, such as the removal of bodily fluids, which may include small particles, from an internal area of an animal body or a human body using an aspirating device, such as an endoscope.

Referring to FIGS. 1-3, at least a portion of the fluid is removed from the fluid source using the aspirating device. The removed or aspirated fluid is transferred through first fluid collection tube 26 into first chamber 40. The aspirated fluid is collected within chamber 40 until a fluid level within first chamber 40 reaches or approaches a fluid level setpoint. The fluid level setpoint is preferably determined and/or calibrated prior to operation of apparatus 10. With the fluid level within first chamber 40 at or near the fluid level setpoint, first level sensor 46 monitors or senses the fluid level and transmits an appropriate signal, such as a stop signal, to relay 48. Relay 48 responsively transmits a signal to first solenoid 45 to close first solenoid valve 44 and prevent communication between vacuum source 42 and first chamber 40. A second signal is preferably simultaneously transmitted from relay 48 to second solenoid 85 to open second solenoid valve 84 and provide communication between vacuum source 42 and second chamber 80.

The operator can continue to aspirate at least a portion of the fluid from the fluid source into second chamber 80 as the aspirated fluid collected in first container 20 is drained into drain pipe 98.

Preferably, the removed or aspirated fluid is transferred from the fluid source through second fluid collection tube 66 into second chamber 80. The aspirated fluid is collected within second container 60 until a fluid level within second chamber 80 reaches or approaches the fluid level setpoint. With the fluid level within second chamber 80 at or near the fluid level setpoint, second level sensor 86 monitors or senses the fluid level and transmits an appropriate signal, such as a stop signal, to relay 48 to close second solenoid valve 84. Relay 48 responsively transmits a signal to solenoid 85 to close second solenoid valve 84 and prevent communication between vacuum source 42 and second chamber 80. First solenoid valve 44 is preferably simultaneously activated by solenoid 45 to open and provide communication between vacuum source 42 and first chamber 40. In one preferred embodiment of this invention, counter 58 counts or records each instance that first solenoid valve 44 and second solenoid valve 84 is activated to close. For example, counter 58 can be activated when a stop signal is transmitted from first level sensor 44 or second level sensor 84 to relay 48.

Thus, this invention provides an apparatus and method for continuously aspirating a fluid from a fluid source. In one preferred embodiment of this invention, each fluid container includes an internally mounted shut-off valve, which monitors the fluid collection for overflow while eliminating the need for operator action, whereby operator contact with or exposure to potentially dangerous or harmful fluid materials and/or medical waste is prevented.

This invention as illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An apparatus for continuously aspirating a fluid from a fluid source comprising:
    a vacuum source;
    a first container forming a first chamber and operatively connected to the vacuum source, a first level sensor positioned within the first chamber and sensing a level of the fluid within the first chamber;
    a second container forming a second chamber and operatively connected to the vacuum source, a second level sensor positioned within the second chamber and sensing a level of the fluid within the second chamber;
    a fluid collection tube providing communication between the fluid source and each of the first chamber and the second chamber; and
    a relay receiving at least one signal from at least one of the first level sensor and the second level sensor, and the relay responsively either activating a first solenoid valve to expose the vacuum source to the first chamber while preventing communication between the vacuum source and the second chamber or activating a second solenoid valve to expose the vacuum source to the second chamber while preventing communication between the vacuum source and the first chamber, to continuously aspirate at least a portion of the fluid from the fluid source.

2. The apparatus of claim 1 further comprising:

the first solenoid valve connecting the first container to the vacuum source and activatable to provide communication between the vacuum source and the first chamber; and the second solenoid valve connecting the second container to the vacuum source, and activatable to provide communication between the vacuum source and the second chamber, the relay in electrical communication with each of the first solenoid valve and the second solenoid valve, the relay receiving the at least one signal and responsively opening one of the first solenoid valve and the second solenoid valve and closing the other of the first solenoid valve and the second solenoid valve.

3. The apparatus of claim 1 further comprising:

a first shut-off valve positioned within the first chamber and preventing communication between the vacuum source and the first chamber with a first fluid level within the first chamber at a first fluid level setpoint; and a second shut-off valve positioned within the second chamber and preventing communication between the vacuum source and the second chamber with a second fluid level within the second chamber at a second fluid level setpoint.

4. The apparatus of claim 3 wherein, with the first shut-off valve prevents communication between the vacuum source and the first chamber, at least a portion of the fluid contained within the first container is drained through a drainage assembly connected to the first container.

5. A method for continuously aspirating a fluid from a fluid source comprising:

aspirating at least a portion of the fluid from the fluid source and into a first chamber formed by a first container, the first chamber in communication with a vacuum source;

collecting the aspirated fluid within the first container until a first level sensor within the first chamber senses a setpoint of a first fluid level;

closing a first solenoid valve by a relay receiving a signal transmitted from the first level sensor to prevent communication between the vacuum source and the first chamber;

opening a second solenoid valve to provide communication between the vacuum source and a second chamber formed by a second container, the second chamber in communication with the vacuum source; and with the first solenoid valve closed, aspirating at least a portion of the fluid from the fluid source and into the second chamber as the aspirated fluid collected in the first container is drained into a drain pipe.

6. The method of claim 5 further comprising:

collecting the aspirated fluid within the second container until a second fluid level within the second chamber approaches a second fluid level setpoint;

closing the second solenoid valve to prevent communication between the vacuum source and the second chamber; and opening the first solenoid valve to provide communication between the vacuum source and the first chamber.

7. The method of claim 5 wherein, upon sensing the first fluid level approaching the first fluid level setpoint, the first level sensor transmits a signal to the relay to close the first solenoid valve.

8. The method of claim 7 wherein, with the first solenoid valve closed, the relay opens the second solenoid valve to provide communication between the vacuum source and the second chamber.

9. The method of claim 6 wherein, upon sensing the second fluid level is approaching the second fluid level setpoint, a second level sensor transmits a second signal to the relay to close the second solenoid valve, and with the second solenoid valve closed, the relay opens the first solenoid valve to provide communication between the vacuum source and the first chamber.

10. The method of claim 6 further comprising the step of counting when each of the first solenoid valve and the second solenoid valve is activated to close.

* * * * *